United States Patent [19]

Helzel

[11] Patent Number: 4,795,427
[45] Date of Patent: Jan. 3, 1989

[54] TWO-COMPARTMENT CATHETER

[76] Inventor: Manfred W. Helzel, Frankenstrasse 29, Würzburg, Fed. Rep. of Germany

[21] Appl. No.: 915,050

[22] Filed: Oct. 3, 1986

[30] Foreign Application Priority Data

Oct. 5, 1985 [DE] Fed. Rep. of Germany ....... 3535641

[51] Int. Cl.$^4$ ............................................. A61M 25/00
[52] U.S. Cl. .................................... 604/53; 604/101; 128/348.1
[58] Field of Search ............... 604/53, 52, 51, 96–103, 604/284; 128/207.15, 344, 348.1, 4

[56] References Cited

U.S. PATENT DOCUMENTS

| | | | |
|---|---|---|---|
| 3,480,017 | 11/1969 | Shute | 128/344 |
| 4,183,102 | 1/1980 | Guiset | 128/344 |
| 4,241,735 | 12/1980 | Chernov | 128/344 |
| 4,423,725 | 1/1984 | Baran et al. | 604/101 |
| 4,581,017 | 4/1986 | Sahota | 604/102 |

FOREIGN PATENT DOCUMENTS 2834956 2/1980 Fed. Rep. of Germany ...... 604/101
0651817 3/1979 U.S.S.R. .............................. 604/101

Primary Examiner—Dalton L. Truluck
Attorney, Agent, or Firm—Fidelman & Wolffe

[57] ABSTRACT

A two-compartment catheter of plastic or rubber is described, which can be introduced into the region of the vena cava where it is joined by the hepatic veins, and serves for therapy of liver diseases and for pharmacological studies on the liver. It consists of a two-lumen catheter which, at one end of the catheter tube, which is to be introduced into the vena cava, has an inflatable elongate extension, the diameter of which at the ends is greater than the diameter in the central region. The inflatable extension has an axially continuous through-flow channel, and the catheter tube leads next to this through-flow channel into a space, separate from the latter, outside the extension.

3 Claims, 2 Drawing Sheets

TWO-COMPARTMENT CATHETER

The invention relates to a two-compartment catheter of plastic or rubber, which can be introduced into the region of the vena cava where it is joined by the hepatic veins, for the therapy of liver diseases and for pharmacological studies on the liver.

In conventional liver therapy, hepatic vein blood is not separated from blood from the vena cava, so that products degraded in the liver can pass into the general blood circulation. A chemotherapeutic treatment therefore frequently has systemic side effects on the total organism. Complicated and lengthy operations are frequently necessary.

It is the object of the invention to provide a catheter which allows a separation of the hepatic vein blood from the vena cava blood and thus makes possible isolated treatment or isolated perfusion of the liver in vivo.

This object is achieved by a two-compartment catheter of the type initially set out, which catheter is designed as a two-lumen catheter which is connected, at one end of its catheter tube, which is to be introduced into the vena cava, to an inflatable elongate extension, the diameter of which at the ends is greater than the diameter in its central region and which has an axial through-flow channel, the catheter tube leading next to the through-flow channel into a space, separate from the latter, outside the extension.

In an advantageous embodiment, the inflatable extension has, on its ends, annular balloons which are mutually connected by an intermediate piece consisting of a cylindrical membrane.

Such a two-compartment catheter is inserted into the vena cava in such a way that the extension bridges the opening region of the hepatic veins in the vena cava. Owing to the inflated end regions or balloons located at the two ends of the extension and exerting a sealing function in the vena cava, the bloodstream of the hepatic veins can be separated from the bloodstream in the vena cava and, therefore, blood originating only from the hepatic veins can be diverted. This allows a selective in vivo diversion of the hepatic vein blood to the outside and a simultaneous passage of the blood from the lower vena cava to the right atrium. In conjunction with two further commercially available catheters, the two-compartment catheter according to the invention thus makes isolated liver perfusion in humans possible. In this way, lengthy operations and/or side effects on the total organism due to chemotherapeutic treatments can be avoided in many cases.

The invention is explained in more detail by reference to two illustrative embodiments shown in the drawings, in which.

The two-compartment catheter according to the invention is a plastic or rubber catheter which is usually about 1 m long and, at one end of its catheter tube 1 or 1a, has a two-lumen inflatable extension 2 or 2a respectively, the diameter of which is greater in the end regions than in its central part. A through-flow channel 3 or 3a leads axially through the extension 2 or 2a respectively.

This extension 2 or 2a is the core piece of the two-compartment catheter, since it serves to provide two separate chambers, on the one hand, in the region of the vena cava consisting of the upper vena cava Vcs and the lower vena cava Vci and, on the other hand, the region where the hepatic veins LeV join. This extension allows a separation and isolated diversion of the hepatic vein blood without thus interrupting the connection between the upper vena cava Vcs and the lower vena cava Vci.

Figure 1:
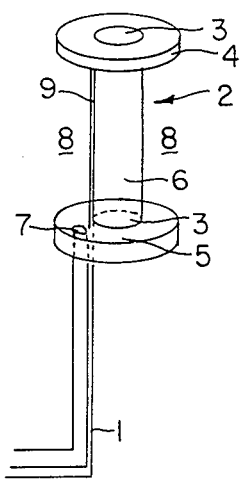
FIG. 1 shows a diagrammatic side view of one embodiment of a two-compartment catheter.
Figure 1A:
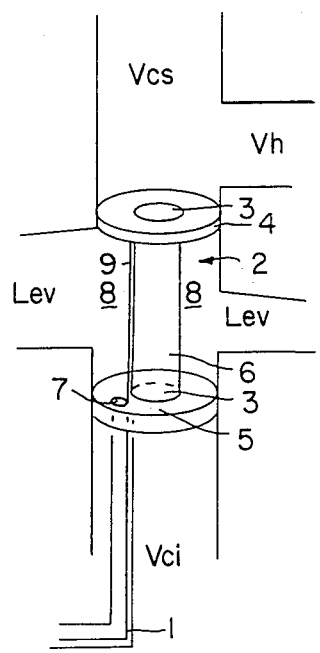
FIG. 1a shows a diagrammatic view of the two-compartment catheter according to FIG. 1, introduced into the region of the vena cava where it is joined by the hepatic veins.
Figure 2:
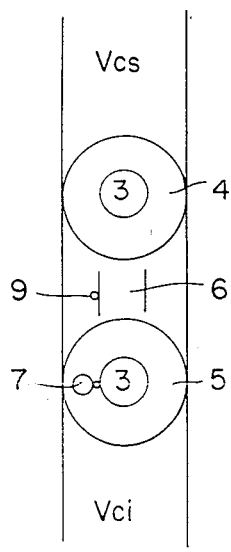
FIG. 2 shows a diagrammatic plan view of the annular balloons with the indicated intermediate piece of the two compartment catheter according to FIGS. 1 and 2.

An advantageous embodiment of the inflatable extension 2 is shown diagrammatically in FIG. 1. It consists of two annular balloons 4 and 5, so-called "twin cuffs", which are arranged at a distance of, for example, 5 to 15 cm and are mutually connected by a cylindrical membrane 6. The balloons 4 and 5, connected by a membrane 6, are inflatable via a channel 9, so that the balloons 4 and 5 bear with their larger diameter against the walls of the venae cavae Vcs and Vci above and below the region where the hepatic veins leV join, and allow sealing of the lumen of the vena cava. The axial through-flow channel 3 here makes the connection between the upper vena cava Vcs and the lower vena cava Vci and forms one compartment of the two-compartment catheter. The cylindrical membrane 6, the diameter of which is smaller than the diameter of the balloons 4 and 5, is located, when the catheter has been introduced and is ready for use, in the region where the hepatic veins LeV join, and separates this region from the remaining lumen of the lower vena cav Vci. The membrane is accordingly surrounded by the second compartment 8 of the two-compartment catheter.

The catheter tube 1 is taken through the balloon 5 adjoining the end of the tube and, outside the cylindrical membrane 6 its orifice 7 leads into the compartment 8, from which hepatic vein blood can be diverted through the catheter tube 1, separately from the vena cava blood.

Figure 3:
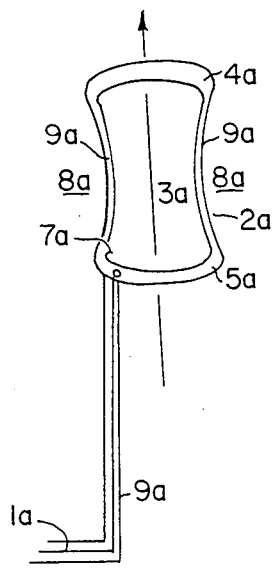
FIG. 3 shows a diagrammatic view of a second embodiment of a two-compartment catheter.
Figure 3A:
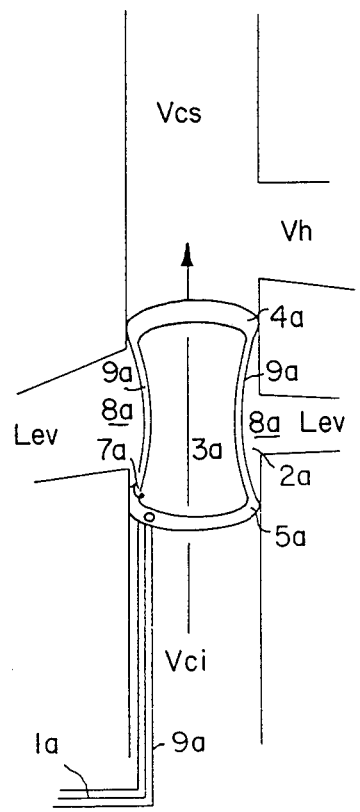
FIG. 3a shows a diagrammatic view of the two-compartment catheter according to FIG. 3, introduced into the vena cava.
Figure 4:
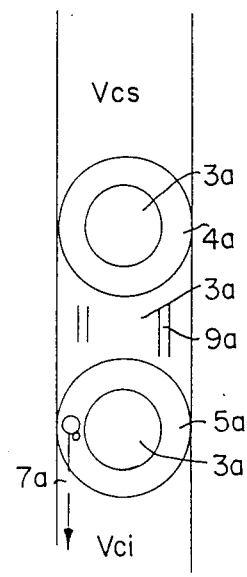
FIG. 4 shows a diagrammatic perspective view of the two ends of large diameter and of a cross-section between these ends of an inflatable extension.

A further embodiment of the twin-lumen catheter according to the invention is shown in FIG. 3. The extension 2a, located on the catheter tube 1a, consists of a body having approximately the shape of a dog's bone and having an axial through-flow channel 3a which forms the first compartment. The hollow end regions 4a and 5a of this extension 2a, which are mutually connected via the channels 9a and are inflatable, have in the inflated state a diameter which is larger than in its center piece. In the same way as in the case of the annular balloons 4 and 5, these end regions 4a and 5a provide sealing in the upper vena cava Vcs and the lower vena cava Vci, whereas the compartment 8a around the narrower center piece of the extension 2a is kept free in the region where the hepatic veins LeV join. In this embodiment, the end of the catheter tube 1a is again taken for a certain length through the interior of the extension 2a and ends in the compartment 8a, for example at 7a. Here again, simultaneous passage of the blood from the lower vena cava Vci to the right atrium Vh is ensured by the selective diversion of the hepatic vein blood to the outside.

The fields of application of the two-compartment catheter are diverse. Thus, in conjunction with a commercially available angiography catheter in the Arteria hepatica and a further catheter in the upper vena cava Vcs, isolated liver perfusion with cytostatic drugs can be carried out for the therapy of primary or secondary malignant liver growths. The cytostatic drugs are extracorporally dialyzed out. The dialyzed blood is reinfused via the third catheter into the upper vena cava.

Further possible applications are the therapy of liver cirrhosis or of hepatic insufficiency and pharmacological in vivo studies on the liver, which have hitherto been virtually impossible.

I claim:

1. A catheter for separating hepatic blood from blood from the vena cava, comprising:
    a tube for obtaining or collecting hepatic blood, said tube being of a size relatively small in diameter relative to the vena cava;
    occluding means for blocking the vena cava on either side of the openings of the hepatic veins into the vena cava and thereby isolating the hepatic blood, said occluding means comprising an at least partially inflatable elongated body attached to one end of the tube and having a central portion and two end portions, said end portions being of a size corresponding to the vena cava when inflated, the diameter of said end portions being greater than the diameter of the central portion so as to provide an annular space between said two end portions isolating said hepatic blood;
    means for allowing blood to flow through the vena cava comprising an axial through-flow channel formed through said inflatable elongated body, said through flow channel receiving blood only from the vena cava; and
    means for communicating with the hepatic blood via said tube, comprising at least one side orifice formed through one of said end portions which communicated with said isolated annular space to obtain or collect the hepatic blood only.

2. A catheter as claimed in claim 1, wherein said end portions of the elongated body each comprise an annular inflatable balloon, said annular inflatable balloons being connected together by a noninflatable cylindrical membrane.

3. A method for separating hepatic blood from blood from the vena cava, comprising:
    inserting into the vena cava an occluding catheter connected to one end of a catheter tube, said catheter comprising an elongaged at least partially inflatable body having a central portion and two end portions, the diameter of said end portions being greater than the diameter of the central portion, said catheter further comprising an axial through-flow channel and a side orifice formed through one of the end portions of the elongated inflatable body;
    placing the catheter within the vena cava so that the two end portions are located on either side of the openings of the hepatic veins into the vena cava;
    inflating the elongated inflatable body so that the two end portions occlude the vena cava above and below the openings of the hepatic veins into the vena cava so that only blood from the vena cava flows through the through-flow channel, and blood from the hepatic veins is separated from the blood of the vena cava and is diverted into the side orifice.

* * * * *